US008859511B2

(12) United States Patent
Nakayama et al.

(10) Patent No.: US 8,859,511 B2
(45) Date of Patent: Oct. 14, 2014

(54) PROLIFERATION INHIBITOR OF HELICOBACTER PYLORI BACTERIA

(71) Applicant: The Noguchi Institute, Tokyo (JP)

(72) Inventors: Jun Nakayama, Matsumoto (JP);
Takashi Shirai, Itabashi-ku (JP);
Takashi Yamanoi, Itabashi-ku (JP);
Masaya Fujita, Itabashi-ku (JP);
Masako Mori, Itabashi-ku (JP)

(73) Assignee: The Noguchi Institute, Tokyo (JP)

( * ) Notice: Subject to any disclaimer, the term of this patent is extended or adjusted under 35 U.S.C. 154(b) by 0 days.

(21) Appl. No.: 13/737,609

(22) Filed: Jan. 9, 2013

(65) Prior Publication Data

US 2013/0131004 A1 May 23, 2013

Related U.S. Application Data

(63) Continuation of application No. 13/063,876, filed as application No. PCT/JP2009/067657 on Oct. 9, 2009, now abandoned.

(30) Foreign Application Priority Data

Oct. 10, 2008 (JP) .................................. 2008-263880

(51) Int. Cl.
*A61K 31/7028* (2006.01)
*A23L 1/09* (2006.01)
*A23L 1/30* (2006.01)
*C07H 15/04* (2006.01)

(52) U.S. Cl.
CPC .............. *A61K 31/7028* (2013.01); *A23L 1/09* (2013.01); *A23L 1/30* (2013.01); *A23V 2002/00* (2013.01); *C07H 15/04* (2013.01); *A23L 1/3018* (2013.01)
USPC .......................................................... 514/42

(58) Field of Classification Search
CPC ...... A23L 1/09; C07H 15/04; A61K 31/7028; A23V 2002/00
USPC .......................................................... 514/42
See application file for complete search history.

(56) References Cited

U.S. PATENT DOCUMENTS

| 2,710,807 | A | 6/1955 | Gyorgy et al. |
| 4,152,513 | A | 5/1979 | Austin et al. |
| 6,756,489 | B1 | 6/2004 | Schmidt et al. |
| 2004/0086514 | A1 | 1/2004 | Ahmed |
| 2009/0054355 | A1 | 2/2009 | Nakayama et al. |
| 2010/0197616 | A1 | 8/2010 | Nakayama et al. |

FOREIGN PATENT DOCUMENTS

| JP | A-2001-512737 | 8/2001 |
| JP | A-2003-517015 | 5/2003 |
| JP | A-2007-246426 | 9/2007 |
| WO | WO 94/03184 A1 | 2/1994 |
| WO | WO 99/007718 | 2/1999 |
| WO | WO 01/43751 A1 | 6/2001 |
| WO | WO 2005/081904 A2 | 9/2005 |
| WO | WO 2008/032817 A1 | 3/2008 |
| WO | WO 2008/084561 A1 | 7/2008 |

OTHER PUBLICATIONS

Apr. 8, 2013 Office Action issued in U.S. Appl. No. 12/662,309.
Miller-Podraza et al. "Novel Binding Epitope for *Helicobacter pylori* Found in Neolacto Carbohydrate Chains," *The Journal of Biological Chemistry*, vol. 280, No. 20, 2005, pp. 19695-19703.
Iwahara et al. "Isolation and Identification of Ethyl-β-Acetylglucosaminide from Yeast Extract," *Biosci. Biotech. Biochem.*, vol. 57, No. 10, 1993, pp. 1779-1780.
Kawagishi et al. "A lectin from an edible mushroom *Pleurotus ostreatus* as a food intake-suppressing substance," *Biochimica et Biophysica Acta*, vol. 1474, 2000, pp. 299-308.
Hiria et al. "Unique Cholesteryl Glucosides in *Helicobacter pylori*: Composition and Structural Analysis," Journal of Bacteriology, vol. 177, No. 18, Sep. 1995, pp. 5327-5333.
Kawakubo et al. "Natural Antibiotic Function of a Human Gastric Mucin Against *Helicobacter pylori* Infection," *Science*, vol. 305, 2004, pp. 1003-1006.
Merriam-Webster Online Dictionary "derivative", available at http://www.merrima-webster.corn/dictionary/derivate, last viewed Aug. 6, 2009.
S. Ebisu et al, Equilibrium Dialysis and Carbohydrate-Building Studies on the 2-Deoxy-DGlucopyranosyl Binding Lectin from Bandeiraea simplicifolia Seeds, Carbohydrate Research vol. 16, 1978 pp. 129-138.
A. Neuberger et al. "Inhibion of Lysozyme by Derivatives of D-Glucosamine. I." Biochim Biophys. Acta. vol. 147, 167 pp. 473-486.
J. Goto et al., Synthesis of Conjugated Cholestrol and Cholestrolas, Chem. Pharm Bull, vol. 27-No. 8, 1979, pp. 1926-1931.
Mar. 20, 2007 International Search Report issued in International Application No. PCT/JP2007/050741.
Oct. 28, 2010 European Search Report issued in Application No. 07710493.3. Hoshino et al., "Search for Aryl N-Acetyl-A-D-Glucosaminides which Suppress the Growth of Helicobacter pylori," Meeting of the Society for Gylcobiology, Universal City, CA, U.S.A., Nov. 15-19, 2006, Oxford University Press, vol. 16, No. 11, p. 1145, Nov. 1, 2006, XP008127483.
Fukuda et al., "Assay of Human Gastric Mucin as a Natural Antibiotic Against Helicobacter pylori," Methods in Enzymology, vol. 415, pp. 164-179, Jan. 1, 2006, XP008127473.
Mayo Clinic Staff, "H. pylori infection," also available at http://www.mayoclinic.com/health/h-pylori/DS00958; last viewed Sep. 28. 2010.

(Continued)

*Primary Examiner* — Brandon Fetterolf
*Assistant Examiner* — Yih-Horng Shiao
(74) *Attorney, Agent, or Firm* — Oliff PLC

(57) ABSTRACT

A method for directly inhibiting proliferation of *Helicobacter pylori* bacteria, that includes administering to a subject infected with *Helicobacter pylori* an N-acetylglucosaminyl beta-linked monosaccharide represented by:

GlcNAcl-beta-O—Y where Y is an alkyl group, an alkoxyl group, an alkenyl group, an alkynyl group, an aralkyl group, an aryl group, a heteroaryl group, a carboxyl group, or an alkoxycarbonyl group.

3 Claims, 4 Drawing Sheets

(56) References Cited

OTHER PUBLICATIONS

Adolfsson et al., "Yogurt and Gut Infection," The American Journal of Clinical Nutrition, vol. 80, pp. 245-256, 2004.
Suerbaum et al., "Medical Progress: Helicobacter Pylori Infection," The New England Journal of Medicine, vol. 347, No. 15, pp. 1175-1186, 2002.
Wood, "Drug Therapy: The Treatment of Helicobacter Pylori Infection in the Management of Peptic Ulcer Disease," The New England Journal of Medicine, vol. 333, No. 15, pp. 984-991, 1995.
Peek Jr. et al. "*Helicobacter Pylori* and Gastrointestinal Tract Adenocarcinomas," Nature Reviews Cancer, vol. 2, 2002, pp. 28-37.
Marshall et al., "Unidentified Curved Bacilli in the Stomach of Patients with Gastritis and Peptic Ulceration," *The Lancet*, vol. 1, 1984, pp. 1311-1315.
Nov. 24, 2009 International Search Report issued in International Application No. PCT/JP2009/067657 (w/ translation).
Nagai, "Clinical and Experimental Studies on Ethyl-N-Acetyl-D-Glucosamine as Bifidus Factor," Paediatria Japonica, Japanese Paediatric Society, vol. 3, No. 6, pp. 83-102, Nov. 1960.
Oct. 14, 2010 Office Action issued in U.S. Appl. No. 12/662,309.
Mar. 30, 2011 Office Action issued in U.S. Appl. No. 12/662,309.
Oct. 10, 2012 Office Action issued in U.S. Appl. No. 12/662,309.

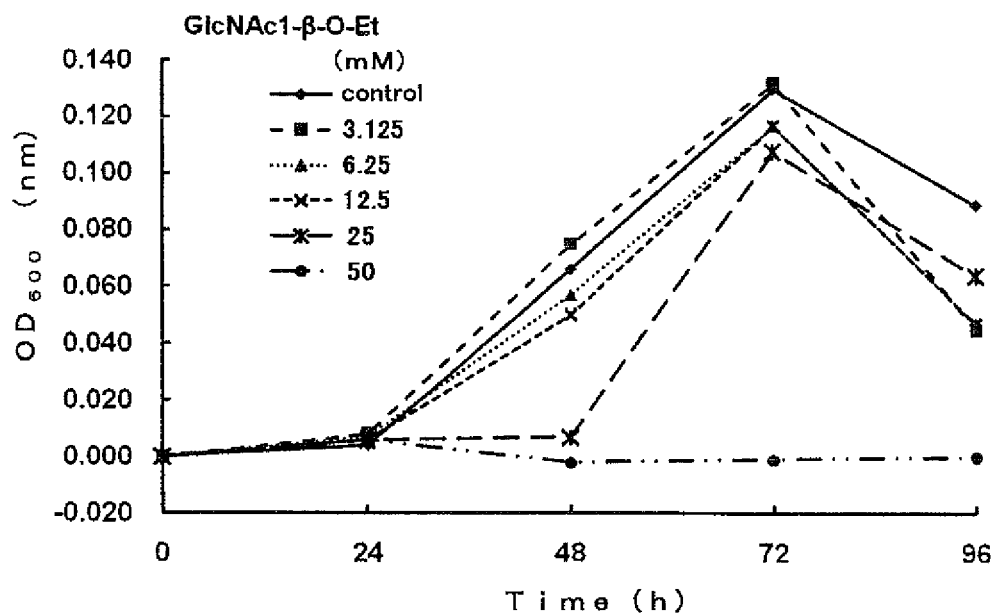
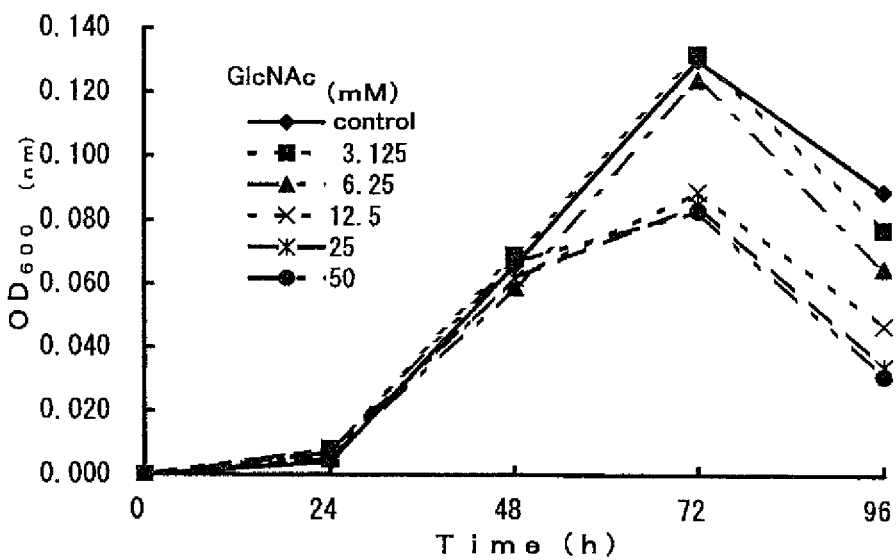

PROLIFERATION INHIBITOR OF HELICOBACTER PYLORI BACTERIA

This is a Continuation of application Ser. No. 13/063,876 filed Jun. 9, 2011, which is a U.S. national stage application of international application PCT/JP2009/067657 filed Oct. 9, 2009, which claims the benefit of JP 2008-263880 filed Oct. 10, 2008. The disclosure of the prior applications is hereby incorporated by reference herein in its entirety.

BACKGROUND

The present invention relates to a proliferation inhibitor of *Helicobacter pylori* bacteria comprising an N-acetylglucosaminyl beta-linked monosaccharide derivative, which can inhibit the proliferation of *Helicobacter pylori* bacteria as a causative microorganism for diseases such as peptic ulcers, gastric cancers and so on.

*Helicobacter pylori* (*H. pylori*) bacteria is a bacteria responsible for peptic ulcers and chronic gastritis (Marshall B. J. et al., Lancet, Vol. I, p. 1311-1315 (1984) and Peek R. M. Jr. et al., Nature Reviews Cancer, Vol. 2, p. 28-37 (2002)). It has been said that the persons infected with *H. pylori* bacteria would reach almost a half of the world population.

*H. pylori* bacteria inhabits in the superficial mucus secreted from the surface layer of the gastric mucous, but never inhabits in the mucous and the glandular mucus secreted from the mucous deep layer. This glandular mucus inherently contains a sugar chain derived from GlcNAc alpha 1-4Gal beta-group-containing O-glycan having a N-acetyl-glucosamine alpha residue (alpha GlcNAc reside) and a galactose residue (Gal residue). For this reason, the foregoing fact would suggest that the sugar chain may protect the gastric mucous from the infection with *H. pylori* bacteria.

The inventors of the present invention found out that a sugar chain of glycoproteins which are each linked with a core binary-branched O-glycan having an alpha GlcNAc residue at the non-reduced terminal can substantially inhibit the proliferation of *H. pylori* bacteria and also that this inhibition of the proliferation is achieved by an enzyme activity inhibition of cholesterol alpha glucosyl transferase (CHL alpha GcT) (Hirai Y. et al., Journal of Bacteriology, Vol. 177, p. 5327-5333 (1995)) which exists only in Helicobacters embracing *H. pylori* bacteria (Kawakubo M. et al., Science, Vol. 305, p. 1003-1006 (2004)). *H. pylori* bacteria essentially requires the glucosyl cholesterol components (CGL) for the proliferation, but it cannot synthesize the CGL by itself. Accordingly, it is said that *H. pylori* bacteria takes in cholesterols from the external world and adds glucose to the region in the proximity to the membrane of the bacterial cell to thus construct the cell wall. In this respect, it would thus be estimated that the foregoing sugar chain of glycoproteins which are each linked with O-glycan carrying the alpha GlcNAc residue has an ability to inhibit the construction of such cell wall, and thus it is expected to be applied to a specific proliferation inbihitor of *H. pylori* bacteria. However, such complicated sugar chain of glycoproteins having high-molecular weight has to be prepared through multiple troublesome steps under a reaction condition which cannot be fully controlled resulting to require extensive manufacturing facilities and great expense. Therefore, it is not practicable.

Moreover, Japanese Patent Provisional Publication (Translation of PCT Application) No. 2003-517015, discloses *Helicobacter pylori* bacteria-binding substances as oligosaccharides comprising Gal beta 1,3 GlcNAc structure. However, such substances are polysaccharides and have quite complicated structure resulting to require multiple steps for preparation which do not permit the mass production of the same.

On the other hand, the presently used methods for treating patients infected with *H. pylori* bacteria are not ones which make use of these sugar chains, but they mainly comprise the step of eradicating bacterial cells through the simultaneous use of the following three kinds of drugs: a kind of proton pump-inhibitor and two kinds of antibiotics. In the medical treatment with which the three kinds of drugs are combined, problems further arise such that this treatment may induce the generation of resistant bacteria to thus cause the recurrence of the infectious disease and that they may cause side effects.

Due to recent increasing concern over health maintenance and harmlessness of beverages, foods or medical preparations, development of a safe proliferation inhibitor of *H. pylori* bacteria having a simple and natural structure which can be continuously eaten, drunk or administrated is desired.

The inventors of the present invention found out that an N-acetylglucosaminyl alpha-linked monosaccharide derivative has a significant effect on inhibiting the proliferation of *H. pylori* bacteria and already filed a patent application (WO2008/084561).

Development of further significant proliferation inhibitor of *H. pylori* bacteria is desired.

SUMMARY

The present invention has been developed to solve the foregoing problems. It is an object of the present invention to provide a proliferation inhibitor of *H. pylori* bacteria comprising a compound that can specifically inhibit the proliferation of *H. pylori* bacteria, which does not generate resistant bacterium, can be eaten, drunken or taken for a long period of time, can be simply mass-manufactured and can be used for beverages, foods or medical preparations.

The inventors of the present invention found out that an N-acetylglucosaminyl beta-linked monosaccharide derivative has more significant effect on inhibiting the proliferation of *H. pylori* bacteria compared to an N-acetylglucosaminyl alpha-linked monosaccharide derivative, and accomplished the present invention.

A proliferation inhibitor of *H. pylori* bacteria of the present invention developed to accomplish the foregoing objects comprises an N-acetylglucosaminyl beta-linked monosaccharide derivative represented by the following chemical formula (1):

GlcNAcl-beta-O—Y    (1)

wherein Y is an alkyl group, an alkoxyl group, an alkenyl group, an alkynyl group, an aralkyl group, an aryl group, a heteroaryl group, a carboxyl group or an alkoxycarbonyl group.

In the chemical formula (1), GlcNAc represents the N-acetyl-glucosaminyl group.

A diet of the food or the beverage of the present invention comprises the foregoing proliferation inhibitor of *H. pylori* bacteria.

The pharmaceutical preparation of the present invention comprises the foregoing proliferation inhibitor of *H. pylori* bacteria.

In the proliferation inhibitor comprising the N-acetylglucosaminyl beta-linked monosaccharide derivative, the monosaccharide derivative reduces an activity of the cholesterol alpha glucosyl transferase (CHL alpha GcT) to inhibit the proliferation of *H. pylori* bacteria, and thus it exerts on an anti-bacterial effect towards *H. pylori* bacteria. When administrating the monosaccharide derivative to human, there is no possibility of generating any resistant bacteria unlike the administration of the antibiotics. The monosaccharide derivative is a glucose derivative having low molecular weight instead of having a complicated chemical structure, so the derivative can be simply produced and is suitable for the industrial production in commercial quantity.

According to the proliferation inhibitor of *H. pylori* bacteria comprising the N-acetylglucosaminyl beta-linked monosaccharide derivative, the monosaccharide derivative inhibits the construction of the cell wall of *H. pylori* bacteria to thus inhibit the proliferation of *H. pylori* bacteria and therefore, it can show a significant pharmaceutical benefit against *H. pylori* bacteria.

In addition, the proliferation inhibitor of *H. pylori* bacteria may comprise the N-acetylglucosaminyl beta-linked monosaccharide derivative alone and/or other drugs such as antibiotics to thus completely remove *H. pylori* bacteria from the stomach and to prevent the recurrence of gastric diseases such as chronic gastritis, peptic ulcers, gastric cancers and/or gastric malignant lymphoma.

Also, the N-acetylglucosaminyl beta-linked monosaccharide derivative inherently exists in living organisms and specifically inhibits the proliferation of *H. pylori* bacteria. Therefore, the proliferation inhibitor comprising thereof would have high safety to the human individual. Furthermore, it has been confirmed that the N-acetylglucosaminyl beta-linked monosaccharide derivative, especially ethyl beta-N-acetylglucosaminide (GlcNAcl-beta-O-Et) is included in yeast extract widely used for food additives. And the yeast extract is considered to be safe foodstuff in view of the food experiences. Therefore, the proliferation inhibitor comprising this derivative can be repeatedly used for a product to be eaten, drunken or administrated for a long period of time.

The diet of the food or the beverage each containing the proliferation inhibitor of *H. pylori* bacteria of the present invention is useful for alleviating the symptoms of gastric diseases, remedying and/or preventing such diseases. This N-acetylglucosaminyl beta-linked monosaccharide derivative shows a strong pharmaceutical effect of inhibiting the proliferation of *H. pylori* bacteria. Consequently, when the proliferation inhibitor of *H. pylori* bacteria is simply incorporated into the diet of these foods and beverages in a small quantity, the resulting diet of the foods and the beverages can show excellent *H. pylori* bacteria-resistant effects.

Moreover, the pharmaceutical preparation comprising the proliferation inhibitor of *H. pylori* bacteria of the present invention is effective for curing, alleviating and/or preventing the gastric diseases caused by the *H. pylori* bacteria such as chronic gastritis and gastric ulcers. The N-acetylglucosaminyl beta-linked monosaccharide derivative shows a strong effect of inhibiting the proliferation of *H. pylori* bacteria and therefore, an excellent *H. pylori* bacteria-resistant effect can be developed simply by administrating a small amount of this pharmaceutical preparation and accordingly, the pharmaceutical preparation is useful for the medical therapy of curing gastric diseases without any side-effects.

BRIEF DESCRIPTION OF THE DRAWINGS

FIG. 1 is a graph showing the *H. pylori* bacteria-resistant effect of a proliferation inhibitor of *H. pylori* bacteria comprising an N-acetylglucosaminyl beta-linked monosaccharide derivative (GlcNAcl-beta-O-Et) to which the present invention is applied.

FIG. 2 is a graph showing the *H. pylori* bacteria-resistant effect of N-acetyl-glucosamine (GlcNAcl) to which the present invention is not applied.

DETAILED DESCRIPTION OF THE EMBODIMENTS

Figure 3:
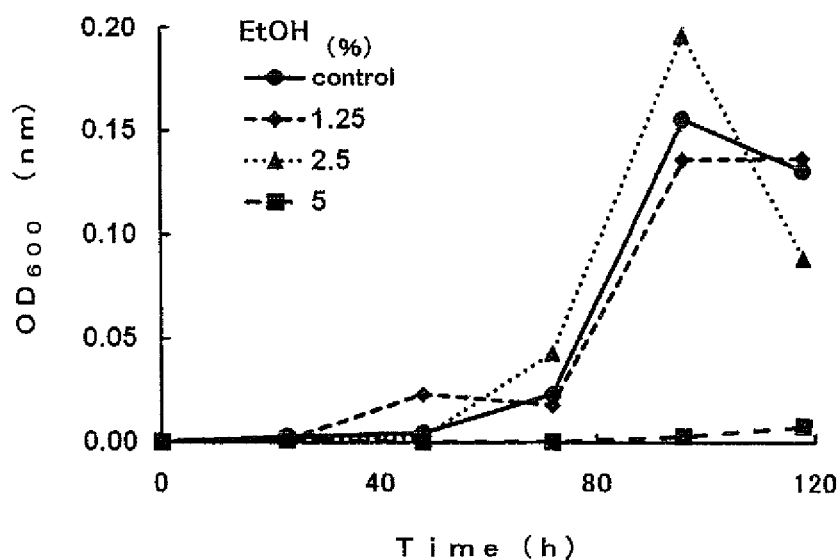
FIG. 3 is a graph showing the *H. pylori* bacteria-resistant effect of ethanol to which the present invention is not applied.

Embodiments according to the present invention will hereunder be described in detail, but the present invention is, by no means, limited to these specific embodiments at all.

The proliferation inhibitor of *H. pylori* bacteria of the present invention comprises an N-ac etylglucosaminyl beta-linked monosaccharide derivative, and it is an effective ingredient for a foodstuff additive or an pharmaceutical preparation. The N-acetylglucosaminyl beta-linked monosaccharide derivative is represented by the foregoing chemical formula (1), or GleNAcl-beta-O—Y, wherein Y is an alkyl group, an alkoxyl group, an alkenyl group or an alkynyl group each having 1 to 27 carbon atoms; an aralkyl group such as benzyl; an aryl group such as phenyl; a heteroaryl group; a carboxyl group; an alkoxycarbonyl group; cholesterol group and so on. More specifically, the derivative has such a structure that the N-acetyl-glucosaminyl group (GlcNAc) is linked by a beta-glycosidic bond.

It is preferable that the proliferation inhibitor of *H. pylori* bacteria is a compound having ethyl group (i.e. GlcNAcl-beta-O-Et) which is included in yeast extract as foodstuff additive. (Iwahara S. et al., Bioscience, Biotechnology, and Biochemistry, Vol. 57, No. 10, p. 1779-1780 (1993)).

The N-acetylglucosaminyl beta-linked monosaccharide derivative, for example GlcNAcl-beta-O-Et, has a significant effect of inhibition of proliferation on *H. pylori* bacteria when used even alone. When a culture medium containing this monosaccharide derivative in a concentration of not less than 5 mM is coexistent with *H. pylori* bacteria, the monosaccharide derivative can control the proliferation ability of *H. pylori* bacteria to a level of not more than 50%. In particular, such culture medium containing the monosaccharide derivative in a concentration of not less than 20 mM thereof can control the proliferation ability of *H. pylori* bacteria to a level of not more than 5%. This monosaccharide derivative is stable in the culture medium and is not decomposed inside the stomach for several hours.

This N-acetylglucosaminyl beta-linked monosaccharide derivative, especially GlcNAcl-beta-O-Et is not only monosaccharide but also a compound simply prepared through a single-step synthetic method and accordingly it can be produced in commercial quantity or scale. In addition, this monosaccharide derivative is quite stable since it is a derivative having an aliphatic hydrocarbon substituent group linked to N-acetylglucosaminyl, and the substituent group through the ether bond is hard to be leaved. Moreover, the aliphatic hydrocarbon group such as an alkyl group is a quite stable residue. This monosaccharide derivative is completely free of any residue harmful to the human individual. Therefore, the safety thereof is considerably high and the monosaccharide derivative can thus be incorporated into the diet of the foods and the beverages as well as pharmaceutical preparations.

These N-acetylglucosaminyl beta-linked monosaccharide derivative are used as the proliferation inhibitor of *H. pylori* bacteria. These saccharide derivatives may be used alone, a plurality of them may be used in combination or they may likewise be used in combination with a kind of proton pump-inhibitor such as Lansoprazole or Omeprazole and two kinds of antibiotics such as Amoxicillin and Clarithromycin.

This proliferation inhibitor of *H. pylori* bacteria comprising the N-acetylglucosaminyl beta-linked monosaccharide derivative may likewise be used as an additive for the diet of the foods and the beverages. In this respect, examples of such diet of the foods and the beverages may be foods, for instance, dairy products such as yoghurt; and beverages such as drink water, cocoa and juices. In this connection, it is preferred to incorporate the N-acetylglucosaminyl beta-linked monosaccharide derivative as an effective component of the proliferation inhibitor of *H. pylori* bacteria into the diet of these foods and beverages in the amount ranging from 0.02 to 1%, more preferably 0.1 to 1%. It is more preferred that the diet of these foods and beverages are those continuously ingested. This is because the *H. pylori* bacteria-proliferation inhibitory effect may further be improved and the continuous ingestion thereof would thus inhibit the peptic diseases, for instance, gastric diseases such as chronic gastritis.

This proliferation inhibitor of *H. pylori* bacteria is used as an effective component to be incorporated into a pharmaceutical preparation. Such the pharmaceutical preparation may be in any form such as a tablet, a capsule, a granule, a pill, an emulsion, a powder, syrup, a liquid preparation, or an injection. Such a pharmaceutical preparation may further comprise components for preparing each pharmaceutical preparation such as excipients, distilled water and physiological saline; and/or other medical components. It is more preferred that these pharmaceutical preparations should be taken once or continuously to thus improve the *H. pylori* bacteria-proliferation inhibitory effect and accordingly, the ingestion thereof would permit the curing or alleviation of the peptic diseases, for instance, gastric diseases such as chronic gastritis.

The following are the description of examples which relate to the synthesis of the N-acetylglucosaminyl beta-linked monosaccharide derivative and the preparation of the proliferation inhibitor of *H. pylori* bacteria of the present invention.

Example 1

1.1 Chemical Synthesis of GlcNAcl-beta-O-Et (2)

Ethoxy-2-acetamide-2-deoxy-N-acetyl-beta-D-glucosaminide (GlcNAcl-beta-O-Et (2)) as an example of the N-acetylglucosaminyl beta-linked monosaccharide derivative represented by the foregoing chemical formula (1) to which the present invention is applied is detailed in this Example 1. This derivative can be synthesized according to the following chemical reaction scheme (3).

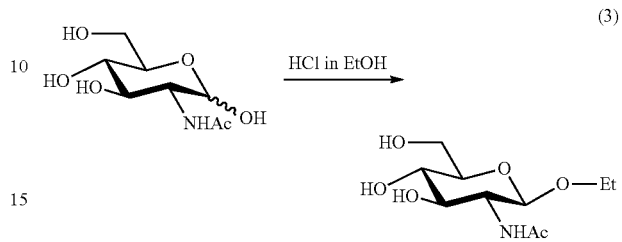

Specifically, 3.0131 g (13.62 mmol) of N-acetyl-D-glucosamine was added to a 200 mL volume eggplant-shaped flask containing HCl gas-bubbled EtOH (50.0 mL) to thus dissolve the compound into the latter, a tube packed with calcium chloride was attached to the flask and the resulting solution was then stirred at room temperature. Whether the reaction was completed or not was confirmed by the thin layer chromatography (TLC) technique (developer solvent: chloroform/methanol (3:1)). After 17 hours, NaHCO$_3$ was added into the reaction mixture to neutralize and then inorganic substances were filtered out through Celite. The filtrate was concentrated and as a result, pink-colored crystals were precipitated. The crystals were purified according to the flash silica-gel column chromatography to thus give white crystalline products of 2.4 g of alpha-derivative in 75% yield and 0.6 g of beta-derivative in 19% yield.

1.2 Identification of GlcNAcl-beta-O-Et (2)

The identification of the product was carried out according to 600 MHz nuclear magnetic resonance (NMR) spectrometry, proving that the stereospecificity of the glycosidic bond is beta (due to J=6.9).

$^1$H-NMR (600 MHz, D$_2$O): δ 1.03 (1H, dd, J=6.9, 7.6 Hz-CH$_2$C$\underline{H}_3$), 1.91 (1H, s, COC$\underline{H}_3$), 3.30 (1H, dd, J=6.9, 9.6 Hz, H-4), 3.31-3.34 (1H, m, H-5), 3.40 (1H, dd, J=8.2, 10.3 Hz, H-3), 3.52-3.56 (2H, m, H-2 and H-6a), 3.62 (1H, dd, J=5.5, 12.4 Hz, CH$_{2a}$CH$_3$), 3.74-3.80 (2H, m, H-6b and CH$_{2b}$CH$_3$), 4.41 (1H, d, J=8.9 Hz, H-1)

$^{13}$C-NMR (150 MHz, D$_2$O); δ 15.3 (—CH$_2$$\underline{C}$H$_3$), 23.2 (CH$_3$CO), 56.7 (C-2), 61.9 (—$\underline{C}$H$_2$CH$_3$), 67.3 (C-6), 71.0 (C-5), 75.1 (C-3), 77.0 (C-4), 101.8 (C-1), 175.7 (CH$_3$$\underline{C}$O)

The spectrographic data clearly support the fact that the beta resulting product is GlcNAcl-beta-O-Et(2).

A proliferation inhibitor of *H. pylori* bacteria comprising thus GlcNAcl-beta-O-Et (2) was prepared and then biological effectivities thereof were evaluated as following deliberate determinations.

Example 2

2.1 Preparation of Proliferation Inhibitor of *H. Pylori* Bacteria Comprising GlcNAcl-beta-O-Et (2) and Confirmation of *H. pylori* Bacteria-Proliferation Inhibitory Effect Under in Vitro The effect of GlcNAcl-beta-O-Et (2) on *H. pylori* bacteria was confirmed according to the following procedures. Bacterial cells of *H. pylori* bacteria (ATCC 43504) stored in a

*brucella* broth culture medium frozen at −80° C. were cultured in the same culture medium (3 mL) supplemented with 10% horse serum at 35° C. in the presence of 15% $CO_2$ for 40 hours according to the shaking culture technique, the movement or behavior of bacterial cells was observed under a microscope and non-coccoid form of *H. pylori* bacteria were recovered. The culture medium was inspected for the optical density (OD) values at 600 nm, followed by the dilution thereof with Muller-Hinton broth culture medium supplemented with 5.5% horse serum such that the number of bacterial cells present therein was equal to $4×10^7$, and 3 mL thereof in total was cultured at 35° C. in the presence of 15% $CO_2$ for 24 hours according to the shaking culture technique, followed by the confirmation of the movement or behavior of bacterial cells by a microscope to thus give an *H. pylori* bacteria-containing culture medium (bacterial cell density: $2×10^7$/mL) used in the test for the confirmation of the effect of the foregoing compound. On the other hand, there were prepared Muller-Hinton broth culture mediums without any bacterial cell of *H. pylori* bacteria each containing 6.25 mM, 12.5 mM, 25 mM, 50 mM and 100 mM of the foregoing GlcNAcl-beta-O-Et and supplemented with 5% horse serum, each of the resulting culture mediums was added to the foregoing *H. pylori* bacteria-containing culture medium in mixing ratio of 1:1 (by volume) (total volume: 1004 each; on a 96-well plate), followed by the mixing there of and the subsequent cultivation at 35° C. in the presence of 15% $CO_2$ for 96 hours. After the cultivation thereof over a predetermined period of time, the bacterial cell density thus proliferated was determined by the measurement of the OD values at 600 nm, followed by the comparison of the result observed for the sample to which the candidate compound was added with that observed for the negative control free of any candidate compound (the control depicted in FIG. 1) to thus evaluate the proliferation inhibitory effect of the compound.

2.2 Effect on Inhibiting the Proliferation of *H. Pylori* Bacteria Under In Vitro The results obtained using GlcNAcl-beta-O-Et are plotted in FIG. 1. As is clear from the data shown in FIG. 1, when adding GlcNAc beta-O-Et in the amount of not less than 25 or 50 mM, it is confirmed that not less than 50% of the *H. pylori* bacteria proliferation is inhibited by the action of the compound.

2.3 Determination of Decomposing GlcNAcl-Beta-O-Et Under In Vitro

GlcNAcl-beta-O-Et in a defined constant amount of the *H. pylori* bacteria-containing culture medium, which was cultured for 3 days, was measured by high performance liquid chromatography. A concentration of GlcNAcl-beta-O-Et therein was determined by conversion using a calibration curve which was beforehand prepared from various definite concentrations of standard GlcNAcl-beta-O-Et and peak areas of high pressure liquid chromatogram thereof. According to the determination, 6% of GlcNAcl-beta-O-Et in the defined constant amount of the *H. pylori* bacteria-containing culture medium was reduced in comparison with initial concentration thereof. Consequently it was obvious that 6% of GlcNAcl-beta-O-Et in the *H. pylori* bacteria-containing culture medium was decomposed to GlcNAc and ethanol (EtOH).

Comparative Example 1

In order to confirm that GlcNAc as a decomposed composition from GlcNAcl-beta-O-Et has no effect on inhibiting the proliferation of *H. pylori* bacteria, incubation of *H. pylori* bacteria as same as protocols of Example 2 was performed by using GlcNAc instead of GlcNAcl-beta-O-Et in Example 2. After incubation for prescribed time, the concentration of proliferated *H. pylori* bacteria was determined by measuring under 600 nm, comparing OD of culture including GlcNAc with OD of culture including no GlcNAc (the control depicted in FIG. 2), and then evaluating the proliferation inhibitory effect of the compound.

The results obtained using GlcNAc are plotted in FIG. 2. As is clear from the data shown in FIG. 2, GlcNAc, which can be produced by the decomposition of GlcNAcl-beta-O-Et, does not show any proliferation inhibitory effect, even when the concentration thereof is extremely high as 50 mM.

Comparative Example 2

In order to confirm that ethanol as a decomposed composition from GlcNAcl-beta-O-Et has no effect on inhibiting the proliferation of *H. pylori* bacteria, incubation of *H. pylori* bacteria as same as protocols of Example 2 was performed by using ethanol of 1.25 volume % (214 mM), 2.5 volume % (428 mM) and 5 volume % (856 mM) instead of using GlcNAcl-beta-O-Et in Example 2. After incubation for prescribed time, the concentration of proliferated *H. pylori* bacteria was determined by measuring under 600 nm, comparing OD of culture including ethanol with OD of culture including no ethanol (the control depicted in FIG. 3), and then evaluating the proliferation inhibitory effect of the compound.

The results obtained using ethanol are plotted in FIG. 3. As shown in FIG. 3, ethanol, which can be produced by the decomposition of GlcNAcl-beta-O-Et, shows proliferation inhibitory effect barely, when the concentration thereof is extremely high as 5 volume %.

Consequently it is obvious that GlcNAcl-beta-O-Et is a pharmacologically active substance in the proliferation inhibitor of *H. pylori* bacteria. And it is obvious that the decomposed substances from GlcNAcl-beta-O-Et do not indicate any pharmacologically activity of inhibiting proliferation of *H. pylori* bacteria.

Example 3

3.1 Preparation of Proliferation Inhibitor of *Helicobacter pylori* Bacteria Comprising GlcNAcl-beta-O-Et (2) and Confirmation of *H. pylori* Bacteria-Proliferation Inhibitory Effect Under In Vivo Antibacterial activities of GlcNAc derivatives towards *H. pylori* bacteria were investigated under in vivo by an experimental system using meriones unguiclatus infected orally with *H. pylori* bacteria.

3.2(1) Animal for the Experiments 4 weeks-old male meriones unguiculatus (SPF: specific-pathogen free), which were purchased from Kyudo Co., Ltd. (Br. Yoshitomi), were preliminarily reared for 23 days and then used for the experiments. The meriones unguiculatus were reared temperature of 24 plus or minus 3° C. and under relative humidity of 55 plus or minus 15% in all room for infected animals with conditions of lighting from a.m. 7 to p.m. 7 and ventilating 18 times per hour during preliminarily reared period and experiment period. 2 or 3 meriones unguiculatus were reared in a cage. All meriones unguiculates could freely get purified water as drinkable water and powdery feed MF as dry feed which is available from Oriental Yeast Co., Ltd. Incidentally the meriones unguiculatus were marked by application of dyestuff of picric acid solution for individual discrimination.

3.2(2) Strain for Infection and Preparation of Bacterial Culture Thereof

Type strain of *H. pylori* bacteria (ATCC 43504 strain) was used as strain for infection. After stock strain thereof was recovered in Brain Heart Infusion (BHI) culture medium, which is available from Nissui Pharmaceutical Co., Ltd., including 10% horse serum, which is available from Dainippon Sumitomo Pharma Co., Ltd., and then cultured in the culture medium at 37° C. under microaerophilic condition using a microaerophilic incubator for 3 days. Finally the concentration thereof was adjusted to approximately $5 \times 10^6$ colony-forming-unit/mL (CFU/mL).

3.2(3) Method for Infection of *Helicobacter Pylori* Bacteria

The meriones unguiculatus were fasted from 24 hours earlier of infection of *Helicobacter pylori* bacteria to 4 hours later of the infection thereof.

Approximately 1.0 mL of the liquid culture medium including *Helicobacter pylori* bacteria was administrated orally as $5 \times 10^6$ CFU/individual-animal to the fasted meriones unguiculatus. The day of infection was defined as initial day (i.e. Day 0)

3.2(4) Preparation and Administration of Specimen

Specimens prepared by using GlcNAcl-beta-O-Et of N-acetyl-glucosamine derivative according to following concentration of each group were administered.

3.2(5) Matter of Each Group

Number of animal: 10 animals per one group
Means for administration: dietary administration
Amount of administration: 0.3% of the specimen blended with the powdery feed

TABLE 1

| Group No. | Group Category (Effective Component) | Number of Animals | Estimated Amount of Administration (mg/kg/day) |
|---|---|---|---|
| 1 | Control | 10 | 0 |
| 2 | GlcNAc1-beta-O-Et | 10 | 300 |

3.3 Inspection Items

3.3(1) Body Weight

Figure 4:
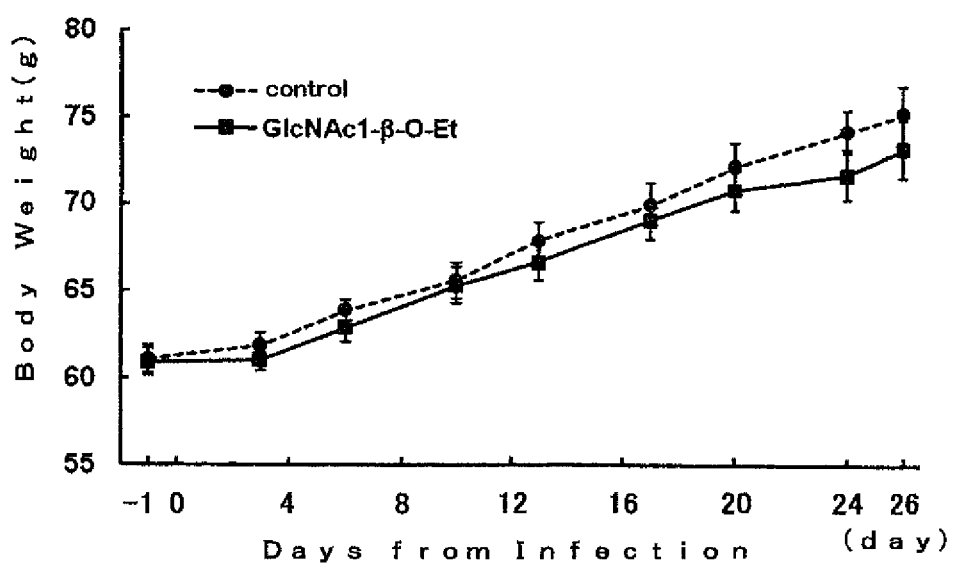
FIG. 4 is a graph showing the body weight change of meriones unguiculatus during the passage of day with or without the administration of the proliferation inhibitor of *H. pylori* bacteria comprising an N-acetylglucosaminyl beta-linked monosaccharide derivative (GlcNAcl-beta-O-Et) to which the present invention is applied.

The day of infection was defined as day 0. At $1^{st}$, $3^{rd}$, $6^{th}$, $10^{th}$, $13^{th}$, $17^{th}$, $20^{th}$, $24^{th}$, and $26^{th}$ days, body weight was measured by a weight scale respectively. The results thereof are shown in FIG. 4.

3.3(2) General Remarks of Symptoms

Daily variance of the general remarks of symptoms thereof was observed.

3.3(3) Determination of Count of Viable Bacteria by Using Count of Colony

Stomach was respectively isolated from thus 10 animals of each group, and added into a centrifuging tube containing 5 mL of a phosphate buffer solution (PBS) to be homogenized with Polytron Homogenizer. 0.1 mL of the obtained homogenate was spread on Poamedia Vi Helico-S agar medium which is available from Eiken Chemical Co., Ltd. And then the bacterium were cultured at 37° C. under microaerophilic condition as same as above-mentioned incubation for culture. The formed violet colonies were counted.

3.4 Statistical Procedure

As regards to body weight and count of colonies, average plus/minus standard error thereof in all groups was respectively calculated. In order to validate statistical significant difference between the control group and each administration group, homoscedasticity thereof was confirmed by Bartlett's test using Analysis Software: Excel Statistics 2006 which is available from Social Survey Research Information Co., Ltd. And then all groups were compared by using Dunnett's test. When the homoscedasticity thereof was not confirmed, the value was performed logarithmic transformation and then all groups were compared by using Dunnett's test. In the both cases, it was considered that $p<0.05$ was statistically significant. The results thereof are shown in FIG. 5.

3.5 Results Under In Vivo

Growth of *H. pylori* bacteria is influenced by environment considerably. Therefore it is necessary that relative comparison between the administration group of the proliferation inhibitor of *H. pylori* bacteria and the non-administration group as the control group should been carried out. As shown in FIG. 4, the statistical significant difference of the body weight increase between the administration group of GlcNAcl-beta-O-Et (2) in the proliferation inhibitor of *H. pylori* bacteria and the non-administration group as the control group was not observed. The abnormal general remarks of symptoms of all animals of both groups could not be observed. The daily amount of administrated GlcNAcl-beta-O-Et is 20 mg/day corresponding to 300 mg/kg/day which is calculated by using daily variance of body weight shown in FIG. 4 and the estimated amount of the administration thereof as shown in Table 1. As shown in FIG. 5(*a*), it is found that GlcNAcl-beta-O-Et (2) reduced the count of *H. pylori* bacteria by ½ to ⅓ in comparison with the control group.

Figure 5:
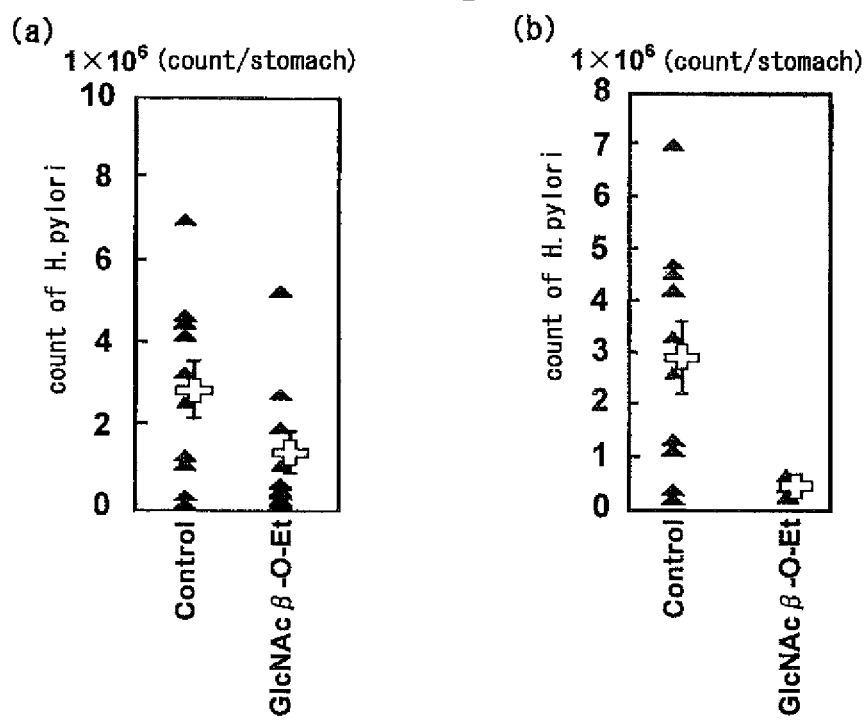
FIG. 5 is a graph showing the count of cultured colonies of *H. pylori* bacteria isolated from exenterated stomach of meriones unguiculatus with or without the administration of the proliferation inhibitor of *H. pylori* bacteria comprising an N-acetylglucosaminyl beta-linked monosaccharide derivative (GlcNAcl-beta-O-Et) to which the present invention is applied.

On the other hand, as shown in FIG. 5(*a*), some individuals in each group have preternaturally high count of *H. pylori* bacteria. The values were considered as outliers. If simply the outliners are omitted, the results may be lack credibility statistically.

Therefore the outliners were strictly rejected by Smirnov-Grubbs test, consequently it is found that on the administration group of GlcNAcl-beta-O-Et (2) in the proliferation inhibitor of *H. pylori* bacteria, the count thereof was reduced by ⅙ in comparison with the control group as shown in FIG. 5(*b*).

Comparative Example 3

Effect on inhibiting the proliferation was investigated as same as Example 2 by using 300 or 1000 mg/kg/day of GlcNAcl-alpha-O-Et instead of 300 mg/kg/day of GlcNAcl-beta-O-Et as administration amount on Example 1 (consultation of Table 1). And determination of body weight, general remarks of symptoms, and count of viable bacteria by using count of colony were also investigated according to above-mentions. They were carried out by above-mentioned statistical procedure. The results of the effect on inhibiting the proliferation are shown in FIG. 6, the results of variance of the body weight are shown in FIG. 7, and the results of the determination of count of viable bacteria are shown in FIG. 8.

Figure 6:
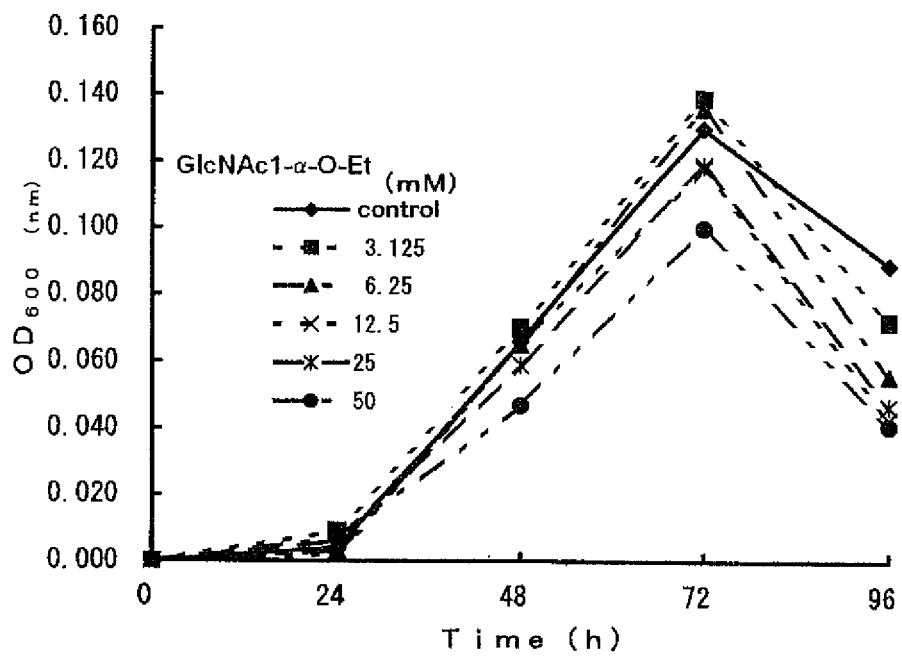
FIG. 6 is a graph showing the *H. pylori* bacteria-resistant effect of an N-acetylglucosaminyl alpha-linked monosaccharide derivative (GlcNAcl-alpha-O-Et) to which the present invention is not applied.

As shown in FIG. 6, GlcNAcl-alpha-O-Et did not almost indicate the effect on inhibiting the proliferation of *H. pylori* bacteria under in vitro in comparison with GlcNAcl-beta-O-Et.

Figure 7:
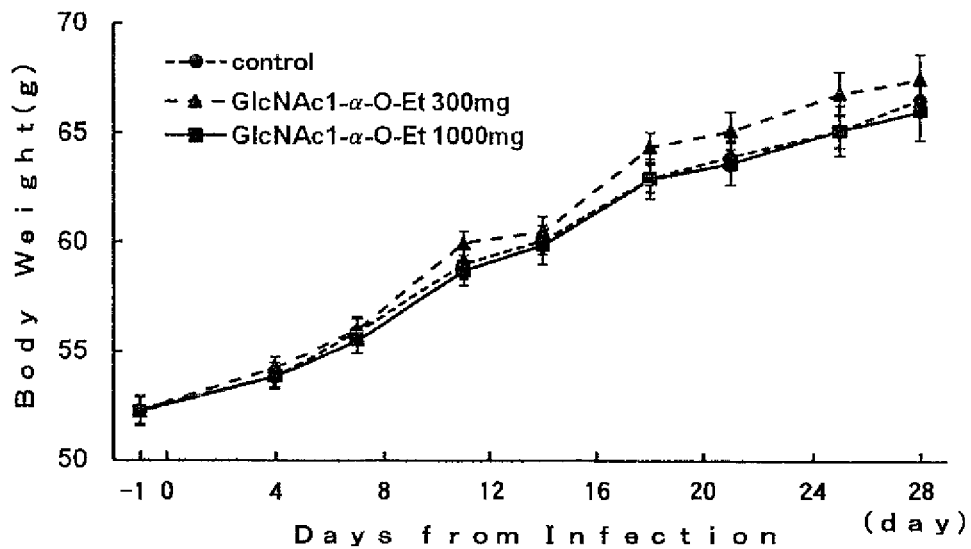
FIG. 7 is a graph showing the body weight change of meriones unguiculatus during the passage of day with or without the administration of the N-acetylglucosaminyl alpha-linked monosaccharide derivative (GlcNAcl-alpha-O-Et) to which the present invention is not applied.

As shown in FIG. 7, the statistical significant difference of the body weight increase between the administration group of GlcNAcl-alpha-O-Et in the proliferation inhibitor of *H. pylori* bacteria and the non-administration group as the control group was not observed.

Figure 8:
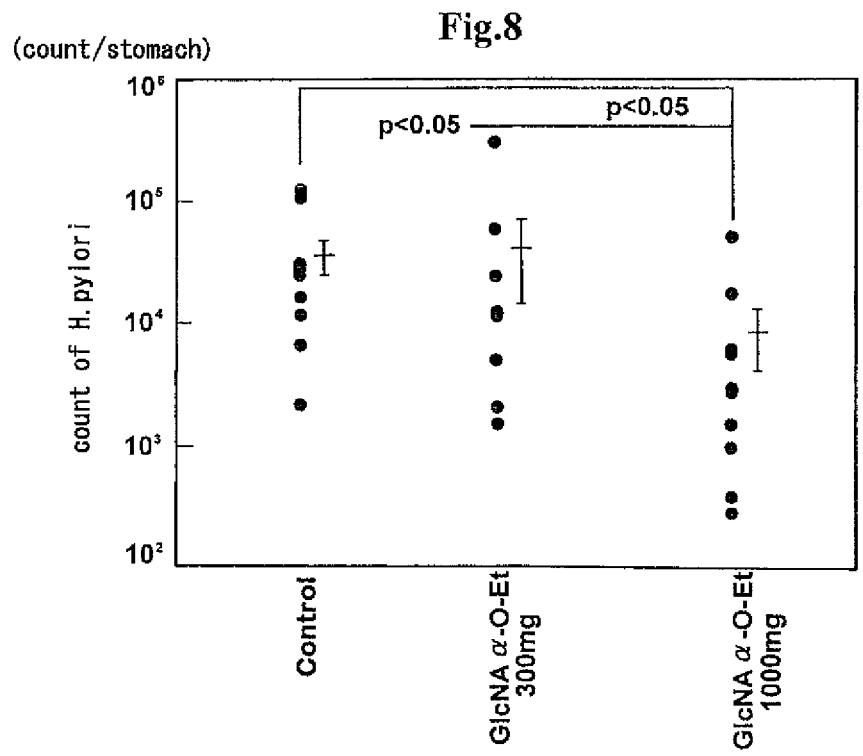
FIG. 8 is a graph showing the count of cultured colonies of *H. pylori* bacteria isolated from exenterated stomach of meriones unguiculatus with or without the administration of the an N-acetylglucosaminyl alpha-linked monosaccharide derivative (GlcNAcl-alpha-O-Et) to which the present invention is not applied.

As shown in FIG. 8, the statistical significant difference of the count of viable bacteria between the administration group of 300 mg/kg/day of GlcNAcl-alpha-O-Et in the proliferation inhibitor of *H. pylori* bacteria and the control group was not observed at all. On the other hand, the statistical significant difference on the administration group of much higher amount as 1000 mg/kg/day of GlcNAcl-alpha-O-Et was eventually observed towards the control group, and the count of *H. pylori* bacteria on the administration group was reduced by ⅓ in comparison with the control group.

Therefore, according to the above-mentioned efforts, it is confirmed that the proliferation inhibitor of *H. pylori* bacteria is useful for the diet of the food or beverage and the pharmaceutical preparation for proliferation inhibitor of *H. pylori* bacteria.

The N-acetylglucosaminyl beta-linked monosaccharide derivative shows its antibacterial effect against *H. pylori* bacteria in such a mechanism that it can inhibit all kinds of proliferative activities essential or indispensable to the growth of the bacterial cells, completely unlike the conventional antibiotics and therefore, it is quite useful as an effective *H. pylori* bacteria-resistant agent.

The proliferation inhibitors of *H. pylori* bacteria comprising these sugar derivatives are effective components for additives for supplements and the diet of the foods and the beverages. The diet of the foods and the beverages each comprising the proliferation inhibitors of *H. pylori* bacteria are useful as functional foods and beverages as well as health foods and beverages. The pharmaceutical preparation comprising the proliferation inhibitors of *H. pylori* bacteria is accordingly useful for curing, alleviation and/or prevention of digestive disease especially gastric disease such as gastritis, gastric ulcer and duodenal ulcer, which are caused by of *H. pylori* bacteria.

What is claimed is:

1. A method for directly inhibiting proliferation of *Helicobacter pylori* bacteria, comprising:
 administering to a subject infected with *Helicobacter pylori* an N-acetylglucosaminyl beta-linked monosaccharide represented by formula (1):

$$\text{GlcNAcl-beta-O—Y} \tag{1}$$

where Y is an alkyl group, an alkoxyl group, an alkenyl group, an alkynyl group, an aralkyl group, an aryl group, a heteroaryl group, a carboxyl group, or an alkoxycarbonyl group.

2. The method of claim 1, wherein the N-acetylglucosaminyl beta-linked monosaccharide is administered to the subject by administering to the subject a food product, a beverage, or a pharmaceutical composition comprising the N-acetylglucosaminyl beta-linked monosaccharide.

3. The method of claim 1, wherein the subject infected with *Helicobacter pylori* is a patient afflicted a gastric disease selected from the group consisting of chronic gastritis, peptic ulcers, gastric cancers, and gastric malignant lymphoma.

* * * * *